United States Patent [19]
Fukuta et al.

[11] Patent Number: 5,756,319
[45] Date of Patent: May 26, 1998

[54] PRODUCTION PROCESS OF S-PHENYL-L-CYSTEINE

[75] Inventors: Kazuhiro Fukuta; Nobuhiro Fukuhara, both of Fukuoka-ken, Japan

[73] Assignee: Mitsui Toatsu Chemicals, Inc., Tokyo, Japan

[21] Appl. No.: 676,666

[22] Filed: Jul. 10, 1996

[30] Foreign Application Priority Data

Jul. 18, 1995 [JP] Japan .................. 7-181537

[51] Int. Cl.⁶ .............. C12P 13/04; C12P 13/12; C12P 9/88
[52] U.S. Cl. .................. 435/106; 435/113; 435/232
[58] Field of Search .................. 435/106, 113, 435/232

[56] References Cited

FOREIGN PATENT DOCUMENTS

| 72935/87 | 2/1988 | Australia. |
|---|---|---|
| 250987 | 1/1988 | European Pat. Off.. |
| 2174390 | 11/1986 | United Kingdom. |

OTHER PUBLICATIONS

Database Biotechnology Abstracts Derwent, AN: 84–00221, XP002016581, JP–A–58146287 and JP–B–02054077, Aug. 1983, Abstracts.

Database WPI, Week 8451, Derwent Publications Ltd., London, GB; AN 84–316062, XP002016582 & JP–A–59198986, Nov. 1984, Abstract.

Chemical Abstracts, vol. 107, No. 15, Oct. 1987, Columbus, OH, US; Abstract No. 132635y, p. 584, Column 132626; XP002016579, Abstract & JP–A–62111694, May 1987.

Chemical Abstracts, vol. 107, No. 19, Nov. 1987, Columbus, OH, US; Abstract No. 174385; XP002016580; Abstract & JP–A–62143690, Jun. 1987.

*Primary Examiner*—Herbert J. Lilling
*Attorney, Agent, or Firm*—Burns, Doane, Swecker & Mathis

[57] ABSTRACT

S-phenyl-L-cysteine can be produced in a high yield by reacting thiophenol and L-serine under the action of tryptophan synthase at a pH in a range of from 9.0 to 10.5. Purification of S-phenyl-L-cysteine obtained by this enzyme reaction can be effectively achieved by adjusting the pH of a crystal-containing reaction mixture to a strongly acidic level of 1.5 or lower to dissolve crystals of S-phenyl-L-cysteine, adding activated carbon to the pH-adjusted mixture, maintaining the resultant mixture at a temperature of from 20° to 60° C. under aeration with an oxygen-containing gas, subjecting the thus-obtained mixture to filtration, raising the pH of the resulting filtrate back to a range of from 2.5 to 6.0 to precipitate crystals of S-phenyl-L-cysteine and then recovering the thus-precipitated crystals.

15 Claims, 2 Drawing Sheets

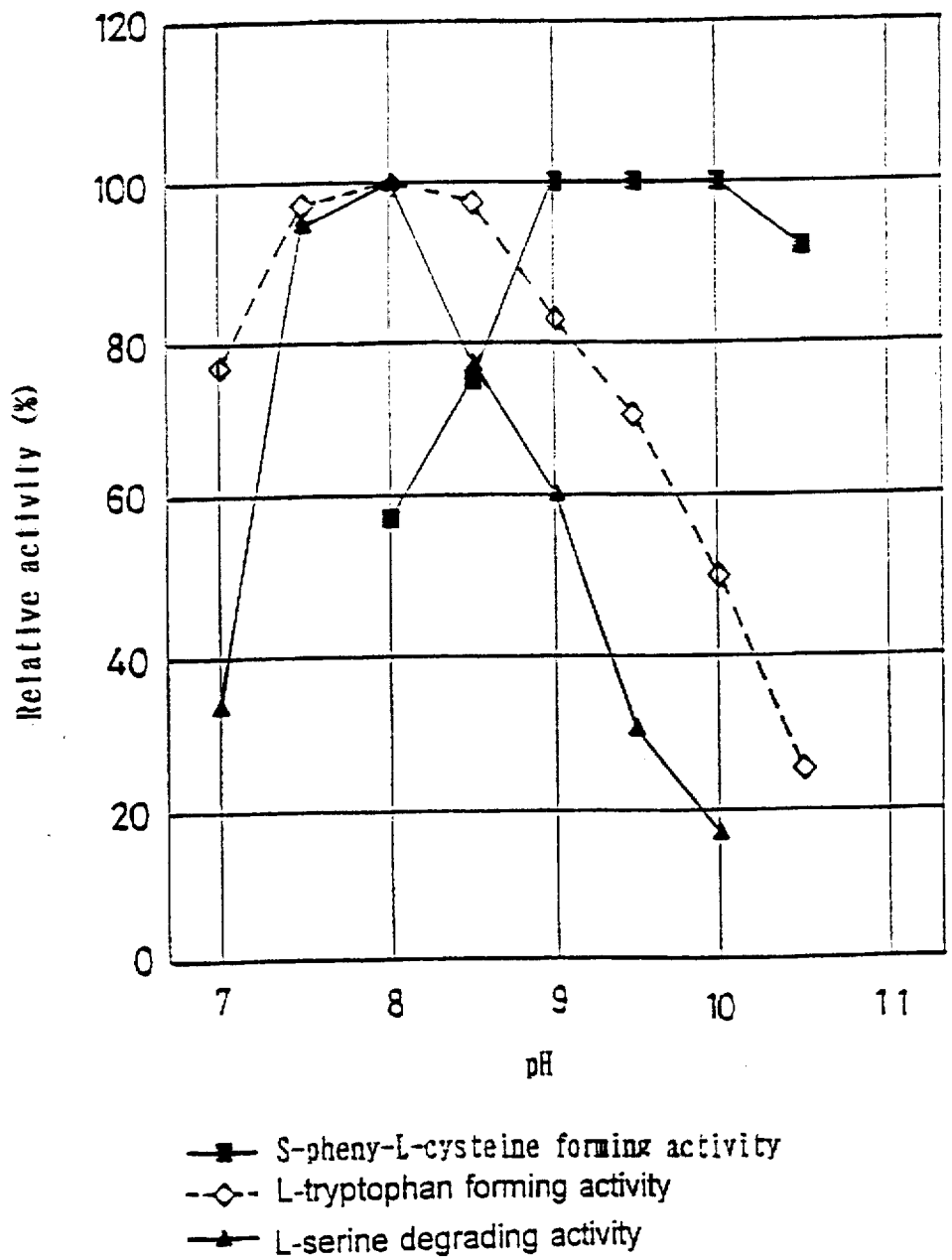

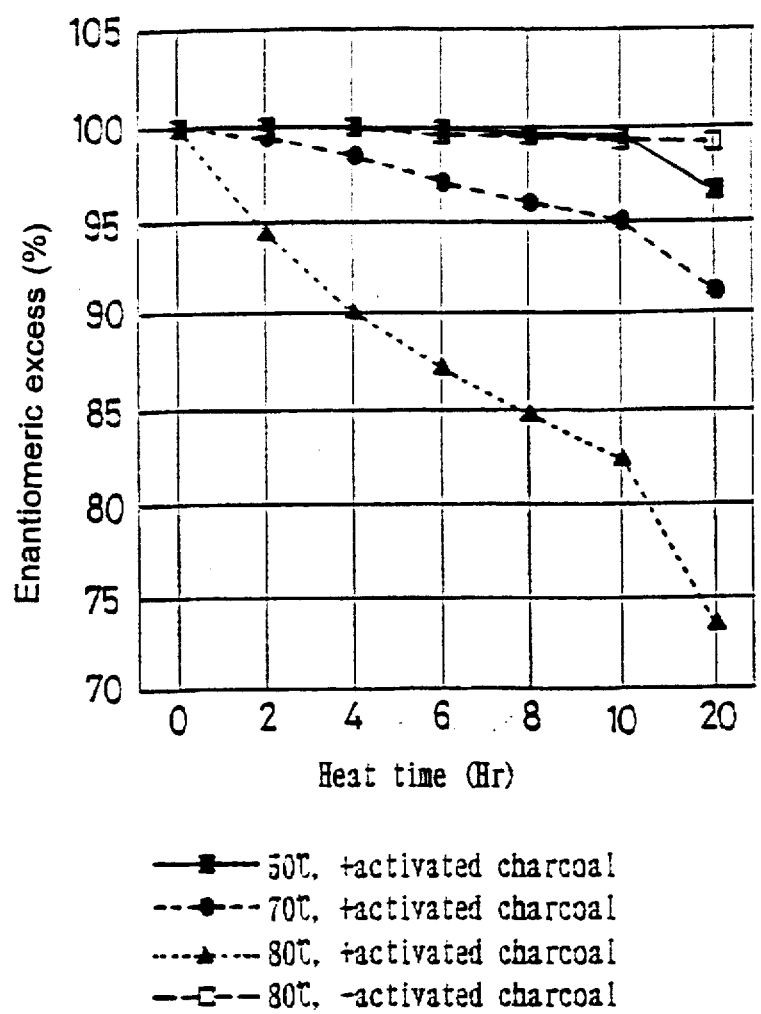

PRODUCTION PROCESS OF S-PHENYL-L-CYSTEINE

BACKGROUND OF THE INVENTION

1. Field of the Invention

This invention relates to a production process of S-phenyl-L-cysteine, and specifically to a process for producing S-phenyl-L-cysteine by reacting thiophenol and L-serine under the action of tryptophan synthase.

2. Description of the Related Art

S-substituted cysteine derivatives are expected to find utility as intermediates for medicines and agrichemicals, so that their synthesis processes have been investigated. No process has however been practiced yet on an industrial scale and the development of an economical production process is therefore desired.

S-phenyl-L-cysteine has recently been found to have utility as a structure of an HIV protease inhibitor, an anti-AIDS drug, or as an amino acid of a constituent of a hydroxyethylamine dipeptide isostere of aspartic protease inhibitors. There is accordingly a desire for the development of a process for the economical and high-purity production of S-phenyl-L-cysteine.

S-phenyl-L-cysteine is known to be synthetically available from L-serine and thiophenol by an enzyme reaction under the action of cysteine desulfhydrase (Japanese Patent Publication No. 13154/1983). In this case, however, the reaction velocity is extremely low so that its practical application is difficult.

S-phenyl-L-cysteine is also known to be synthetically available from L-serine and thiophenol by an enzyme reaction under the action of tryptophan synthase (Japanese Patent Publication No. 54077/1990). Here again, the reaction yield is low, thereby failing to achieve any yield sufficient to justify its industrialization.

As has been described above, the process for producing S-phenyl-L-cysteine from L-serine and thiophenol by using cysteine desulfhydrase or tryptophane synthase has not been developed beyond a laboratory level and has not achieved any yield sufficient for its industrial application.

SUMMARY OF THE INVENTION

An object of the present invention is to provide a process which can produce S-phenyl-L-cysteine in a high yield.

The present inventors have proceeded with an extensive investigation to seek a process for producing S-phenyl-L-cysteine by using tryptophan synthase. As a result, it has been surprisingly found that the yield of S-phenyl-L-cysteine can be unexpectedly increased by conducting an enzyme reaction in an alkaline aqueous solution having the selected pH range upon reacting thiophenol and L-serine under the action of tryptophan synthase, leading to the completion of the present invention.

The present invention therefore provides a process for producing S-phenyl-L-cysteine by reacting thiophenol and L-serine under the action of tryptophan synthase, wherein said reaction is conducted in an aqueous solution of a pH in a range of from 9.0 to 10.5.

In industry, tryptophan synthase is generally known as an enzyme for synthesizing L-tryptophan from indole and L-serine. In this case, the optimal pH is generally known to range from 8.0 to 8.5

In the case of the enzyme reaction for the synthesis of S-phenyl-L-cysteine from thiophenol and L-serine, the present inventors have, however, been found that, although it is an enzyme reaction making use of the same tryptophan synthase, neither sufficient reaction velocity nor sufficient yield can be obtained unless the reaction is conducted under alkaline conditions of pH 9.0 to pH 10.5 which is excluded from the above well-known optimum pH range (pH 8.0 to pH 8.5).

A process according to one embodiment of the present invention for the production of S-phenyl-L-cysteine comprises a step in which thiophenol and L-serine are reacted under the action of tryptophan synthase in an aqueous solution at a pH in a range of from 9.0 to 10.5 to form S-phenyl-L-cysteine.

A process according to another embodiment of the present invention for the production of S-phenyl-L-cysteine comprises the following steps:

(a) adjusting the pH of an enzymatic reaction mixture containing crystals of S-phenyl-L-cysteine to an acidic level so that the crystals of S-phenyl-L-cysteine precipitated in said reaction mixture are dissolved;

(b) adding activated carbon to said reaction mixture, in which S-phenyl-L-cysteine is dissolved, and then maintaining the resultant reaction mixture while aerating the same with an oxygen-containing gas;

(c) removing said activated carbon and insolubilized matter from said reaction mixture to obtain an S-phenyl-L-cysteine solution; and (d) raising the pH of said S-phenyl-L-cysteine solution back to a range of from 2.5 to 6.0 to precipitate crystals of S-phenyl-L-cysteine, and then recovering said crystals of S-phenyl-L-cysteine.

According to the present invention, S-phenyl-L-cysteine can be obtained in a high yield, thereby enabling the production on an industrial scale.

BRIEF DESCRIPTION OF THE DRAWINGS

FIG. 1 is a diagrammatic representation of effects of pH on individual enzyme activities obtained in Experiment 1; and FIG. 2 is a diagrammatic representation of effects of temperature on optical purities obtained in Experiment 2.

DETAILED DESCRIPTION OF THE INVENTION AND PREFERRED EMBODIMENTS

A producer microorganism for tryptophan synthase employed in the process of this invention can be a procaryotic microorganism such as *Escherichia coli* or a transformed microorganism created by applying recombinant DNA technology and imparted with enhanced productivity of the enzyme. As an alternative, the tryptophan synthase can also be that obtained from *Saccharomyces cerevisiae* or a eucaryotic microorganism such as a fungus, or a transformed microorganism created by applying recombinant DNA technology to enhance the productivity of the enzyme by the eucaryotic microorganism.

Preferred are *Escherichia coli* MT-10242 (FERM BP-20), *Neurospora crassa* ATCC 14692 and the like. More preferred is a microorganism having tryptophan synthase activity sufficient to synthesize 1 g of tryptophan in an hour per gram of dry cells of the microorganism.

*Escherichia coli* MT-10242 (FERM BP-20) has been disclosed in the granted Japanese Patent Applications, i.e., Japanese Patent Publication (Kokoku) Nos. 25353/87 and 55669/92, and its sample is publicly available from the National Institute of Bioscience and Human-Technology of the Agency of Industrial Science and Technology; 1-3, Higashi 1-chome, Tsukuba-shi, Ibaraki-ken, 305, Japan.

As a medium for culturing a tryptophan-synthase-producing microorganism, either a synthetic culture medium or a natural culture medium is usable provided that it contains a carbon source, a nitrogen source, inorganic substances, and small amounts of trace nutrients as needed. However, it is generally necessary to add tryptophan, anthranilic acid or indole in a small amount to the culture medium. Any carbon source and nitrogen source can be used in the culture medium insofar as they can be assimilated by the selected microorganism. Examples of the carbon source include various hydrocarbons such as glucose, glycerol, fructose, sucrose, maltose, mannose, starch, starch hydrolysate and treacle. Examples of the nitrogen source include ammonia; various inorganic or organic ammonium salts such as ammonium chloride, ammonium sulfate, ammonium carbonate and ammonium acetate; and natural organic nitrogen sources such as meat extract, yeast extract, corn steep liquor, casein hydrolysate, fish meal or its digest, and defatted soybean meal or its digest. Many of natural organic nitrogen sources can each become both a nitrogen source and a carbon source. As inorganic substances, potassium monohydrogenphosphate, potassium dihydrogenphosphate, potassium chloride, magnesium sulfate, sodium chloride, ferrous sulfate and the like can be used as needed.

Culturing is conducted under aerobic conditions, for example, by shaking culture or submerged aeration-agitation culture. The culturing temperature is in a range of from 20° to 50° C., usually in a range of from 30° to 37° C. During the culturing, it is desired to maintain the pH of the culture medium around the neutral level. The culturing time generally ranges from 1 to 3 days.

An extraction method of tryptophan synthase from cultured cells of *Escherichia coli* is disclosed in The Journal of Biological Chemistry, 252(19), 6594–6599, 1977, while an extraction method of the same enzyme from cultured cells of *Neurospora crassa* is disclosed in ibid., 250(8), 2941–2946, 1975. It is however to be noted that tryptophan synthase to be used in the present invention is not absolutely required to be pure. Namely, a cultured medium of a tryptophan-synthase-producing microorganism, viable cells collected by centrifugation or the like from such a cultured medium, dried cells obtained by drying such viable cells, a processed or treated cell product-obtained by subjecting such cells to disruption, autolysis or ultrasonic treatment, an extract of such cells, and a crude product of the enzyme obtained from such an extract are all usable. They can each be in the form of an immobilized enzyme or immobilized cells.

In the present invention, the raw materials for the synthesis of S-phenyl-L-cysteine by the enzyme reaction are L-serine and thiophenol, which are both commercially marketed and readily available.

Although no particular limitation is imposed on the concentration of L-serine in the reaction mixture, its concentration preferably ranges from 1 to 10 wt. %.

The concentration of thiophenol in the reaction mixture must be in a range in which it does not adversely affect the enzyme reaction. Thiophenol is preferably employed at a concentration of 10 wt. % or lower. Incidentally, thiophenol can be added successively in portions in the course of the reaction.

Upon conducting the reaction, it is desired to incorporate, in addition to a substrate, pyridoxal phosphate in a range of from 0.1 to 100 ppm.

The amount of tryptophan synthase to be added to the reaction mixture can be varied as needed depending on the concentration of the substrate, the reaction time and other conditions.

The enzyme reaction for the synthesis of S-phenyl-L-cysteine according to the present invention is conducted under alkaline conditions of from pH 9.0 to pH 10.5. Particularly preferred is a pH range from 9.0 to 10.0. Examples of an alkali include sodium hydroxide, potassium hydroxide and aqueous ammonia.

If the pH is lower than 9.0, the velocity of the enzyme reaction for the synthesis of S-phenyl-L-cysteine is extremely low so that L-serine, one of the raw materials, cannot be converted sufficiently into S-phenyl-L-cysteine. Especially when tryptophan synthase is not used in a pure form, use of a pH lower than 9.0 results in a degradation velocity of L-serine higher than a synthesis velocity of S-phenyl-L-cysteine because a microorganism contains one or more enzymes having L-serine degrading activity. The degradation of L-serine as one of the raw materials therefore proceeds preferentially, leading to the production of S-phenyl-L-cysteine in a low yield. Incidentally, addition of an ammonium salt can reduce the L-serine degrading activity, but is not significantly effective because the velocity of the enzyme reaction for the synthesis of S-phenyl-L-cysteine is low if the pH is lower than 9.0.

In the pH range of from 9.0 to 10.5, the velocity of the enzyme reaction for the synthesis of S-phenyl-L-cysteine unexpectedly increases and on the other hand, the degrading velocity of L-serine conveniently drops, whereby the formation of S-phenyl-L-cysteine proceeds preferentially. Accordingly, in the reaction at pH 9.0 to 10.5, the reaction yield of S-phenyl-L-cysteine is significantly improved. If the pH exceeds 10.5, however, the velocity of the enzyme reaction for the synthesis of S-phenyl-L-cysteine is lowered again so that its yield decreases.

Even when the enzyme reaction is conducted at pH 9.0 or higher, addition of an ammonium salt for the purpose of reducing the L-serine degrading activity of an enzyme or enzymes is preferred from the standpoint of increasing the reaction yield. Usable examples of the ammonium salt include ammonium chloride, ammonium sulfate, ammonium nitrate and ammonium acetate.

The enzyme reaction according to the present invention is conducted generally at a temperature in a range of from 20° to 60° C. From the standpoint of the stability of the enzyme and the reaction velocity, the reaction temperature is preferably from 30° to 40° C.

Further, with a view to preventing oxidation of thiophenol, it is preferred to conduct the reaction in an anaerobic atmosphere.

The reaction can be conducted either under quiescent conditions or under agitation and either by a batch process or by a continuous process in which the enzyme is used in an immobilized form. When the reaction is conducted at a thiophenol concentration of 5 wt. % or higher, application of gentler agitation leads to a better reaction yield.

When the reaction is conducted at a thiophenol concentration of from 5 wt. % to 10 wt. %, it is desired to conduct the reaction while controlling the agitation power for the reaction mixture at 20 KW/m$^3$ or lower, preferably within a range of from 5 KW/m$^3$ to 16 KW/m$^3$.

The reaction time usually ranges from 5 to 40 hours.

S-Phenyl-L-cysteine has a low solubility in water so that in general, S-phenyl-L-cysteine progressively precipitate as crystals in the reaction mixture as the enzyme reaction proceeds.

To obtain S-phenyl-L-cysteine in a purified form from the reaction mixture subsequent to the completion of the enzyme reaction, the pH of the reaction mixture is adjusted to an acidic side with an appropriate acid such as hydrochloric acid or sulfuric acid so that the crystals precipitated in the reaction mixture are dissolved. The reaction mixture is then subjected to adsorption treatment with activated carbon or the like, whereby microorganism cells or the enzyme and the unreacted thiophenol are removed. Subsequent pH shift with an appropriate alkali causes S-phenyl-L-cysteine to precipitate as crystals, so that S-phenyl-L-cysteine can be easily isolated by filtration or the like.

When the reaction mixture is acidified after the completion of the reaction to dissolve the crystals of S-phenyl-L-cysteine, it is preferred to control the pH to an acidic condition of pH 1.5 or lower in order to improve the solubility of S-phenyl-L-cysteine; for example its concentration can be 1 wt. % or higher and the volumetric efficiency can be improved.

To remove the enzyme or the microorganism cells or microorganism-derived cell components and the unreacted thiophenol after the crystals of S-phenyl-L-cysteine precipitated in the reaction mixture are dissolved, adsorption treatment with activated carbon is conducted. In this case, the enzyme or the microorganism cells or microorganism-derived cell components and the unreacted thiophenol can be removed from the solution of S-phenyl-L-cysteine by adding activated carbon to the solution in which S-phenyl-L-cysteine has been dissolved under acidic conditions, preferably heating the resultant mixture to 20° to 60° C. to adsorb the enzyme or the microorganism cells or microorganism-derived cell components and the unreacted thiophenol on the activated carbon and then by conducting a separating operation such as filtration or centrifugation. Usable examples of the activated carbon include "PM-SX", "PM-PA", "PM-KI", "PM-KS" and "PM-AA" (trade names, products of Mitsui Pharmaceutical, Inc.); "WPH", "PCB-G" and "ADP" (trade names, products of Calgon Far East Co., Ltd.); "Shirasagi A", "Shirasagi M", "Shirasagi C" and "Carbolaphin" (trade names, product of Takeda Pharmaceutical Industries, Ltd.); and "Taiko S Type" and "Taiko K Type" (trade names; Futamura Chemical Industries Co., Ltd.). Activated carbon is usually added in an amount of 0.5 to 6 wt. % based on the weight of the reaction mixture. It is however possible to change the amount of activated carbon in accordance with the amount of the enzyme or microorganism cells employed as a tryptophan synthase source in the enzyme reaction and the amount of unreacted thiophenol.

It is preferred to add activated carbon to the reaction mixture in an amount up to three fold amount of the S-phenyl-L-cysteine. If the amount of activated carbon is higher than the thrice amount of that of S-phenyl-L-cysteine, adsorption of S-phenyl-L-cysteine to activated carbon becomes remarkable.

Unreacted thiophenol still remains in the solution in which the crystals of S-phenyl-L-cysteine deposited during the enzyme reaction have been dissolved under acidic conditions. A portion of the unreacted thiophenol is adsorbed on activated carbon upon treatment with the activated carbon, but the unreacted thiophenol is not completely removed by adsorption. It is however possible to remove the remaining unreacted thiophenol if upon conducting the treatment with activated carbon, the solution is aerated with air or oxygen, because thiophenol unadsorbed on the activated carbon is oxidized into an insoluble solid and is hence removed by filtration. In particular, the aeration at a temperature of 20° C. or higher than 20° C. can provide a higher efficiency in oxidation of thiophenol. Preferable aeration rate of the gas to the solution may range from 0.01 to 6.0 vol/vol. per hour.

Concerning the temperature upon conducting the treatment with activated carbon, it is further preferred to conduct the treatment with activated carbon at 20° to 60° C. because racemization of S-phenyl-L-cysteine becomes significant if the temperature exceeds 60° C. Especially, it is necessary to avoid unnecessarily long contact with activated carbon under heat because racemization is promoted when heated in the presence of activated carbon. For the above reason, the time of contact with activated carbon is preferably 12 hours or shorter.

To obtain S-phenyl-L-cysteine as crystals from the acidic solution of S-phenyl-L-cysteine from which the enzyme or the microorganism cells or microorganism-derived cell components and the unreacted thiophenol have been removed, crystallization by adding an appropriate alkali may be used. When the pH is controlled to 2.5 to 6.0 upon conducting crystallization, pure white crystals are obtained. If the crystallization is conducted at pH 6 to pH 7, the resulting crystals may be tinted with a gray to yellow color. Usable examples of the alkali for the pH shift include sodium hydroxide, potassium hydroxide, aqueous ammonia, potassium pyrophosphate and sodium pyrophosphate.

The present invention will hereinafter be described in detail by the following examples.

Incidentally, quantitations of S-phenyl-L-cysteine and L-serine were conducted by HPLC. Conditions for HPLC analysis of S-phenyl-L-cysteine:

Column: "Inertsil ODS-2" (trade name, product of GL Sciences Inc.).

Mobile phase: 8.6 mM $KH_2PO_4$ (conditioned with phosphoric acid of pH 4)/$CH_3OH$=7/3

Temperature: 40° C.

Flow rate: 1.0 ml/min

Detection: 254 nm UV

Conditions for HPLC analysis of L-serine:

Column: "Shodex RSpak NN-814" (trade name, product of Showa Denko K.K.)

Mobile phase: 10 mM $NaH_2PO_4$ +1.2 mM phosphoric acid

Temperature: 40° C.

Flow rate: 1.0 ml/min

Detection: OPA reagent Ex=365 nm, Em=455 nm

Experiment 1

*Escherichia coli* MT-10242 (FERM BP-20), tryptophan-synthase-producing bacterium, was inoculated to a 500-ml shouldered flask (Sakaguchi flask), which contained 150 ml of a culture medium having the composition shown in Table 1. The bacterium was subjected to shaking culture at 30° C. for 24 hours. The cultured medium (600 ml - equivalent to 4 flasks) were inoculated to a 20-l jar fermenter in which 10 l of a culture medium having the composition shown in Table 2 had been charged, followed by aeration culture at 30° C. and pH 6.8 (controlled with concentrated aqueous ammonia) for 40 hours while successively adding glucose. After completion of the culturing, cells were collected by centrifugation and the wet cells so obtained were provided as a tryptophan synthase source.

L-tryptophan forming activity, S-phenyl-L-cysteine forming activity and L-serine degrading activity of the cells were each measured by changing the pH of the reaction mixture.

These activities at varied pHs are shown in FIG. 1.

I. Method for the measurement of L-tryptophan forming activity

Prepared reagent 1: L-serine solutions

L-serine solutions of varied pHs in a range of from 7 to 11 were each prepared by dissolving 10.6 g of L-serine in about 450 ml of purified water, adjusting the pH of the resultant solution to the corresponding pH with an aqueous solution of potassium hydroxide and then adding purified water to give a total volume of 500 ml.

Prepared reagent 2: PLP solutions

PLP solutions of varied pHs in a range of from 7 to 11 were each prepared by dissolving 50 mg of pyridoxal phosphate in about 950 ml of purified water, adjusting the pH of the resultant solution to the corresponding pH with an aqueous solution of potassium hydroxide and then adding purified water to give a total volume of 1,000 ml.

Cell suspension:

Wet cells (1 g) were suspended in 10 ml of a PLP solution whose pH had been adjusted to 8.5.

Measuring procedures:

Indole (0.4 g) was weighed in a 100-ml Erlenmeyer flask. "Triton X-100" (1 ml) was added, followed by heating to dissolve the indole. The resultant mixture was added with 18 ml of one of the L-serine solutions and 0.5 ml of one of PLP solutions. After the mixture so obtained was incubated at 35° C. for 5 minutes, 0.5 ml of the cell suspension was added, followed by incubation at 60 minutes under shaking. Sixty minutes later, 10 ml of 5N NaOH were added to terminate the reaction and 0.5 ml of phosphoric acid was added to neutralize the reaction mixture. A portion (1 ml) of the solution was sampled in a microtube. Dichloromethane (1 ml) was added, followed by thorough mixing. The resultant mixture was then centrifuged into an aqueous phase and an organic phase. The concentration of L-tryptophan in the aqueous solution was quantitated by HPLC. Conditions for the HPLC analysis of L-tryptophan were the same as those employed for the HPLC analysis of S-phenyl-L-cysteine. The amount (g) of L-tryptophan formed in an hour per gram of the dried cells was defined as L-tryptophan forming activity.

II. Method for the measurement of S-phenyl-L-cysteine forming activity

Prepared reagent 1: L-serine solutions

L-serine solutions of varied pHs in a range of from 7 to 11 were each prepared by dissolving 15.5 g of L-serine and 5.6 g of ammonium chloride in about 450 ml of purified water, adjusting the pH of the resultant solution to the corresponding pH with an aqueous solution of sodium hydroxide and then adding purified water to give a total volume of 500 ml.

Prepared reagent 2: PLP solutions

PLP solutions of varied pHs in a range of from 7 to 11 were each prepared by dissolving 50 mg of pyridoxal phosphate in about 15 ml of purified water, adjusting the pH of the resultant solution to the corresponding pH with an aqueous solution of sodium hydroxide and then adding purified water to give a total volume of 20 ml.

Cell suspension:

Wet cells (1 g) were suspended in 10 ml of a PLP solution whose pH had been adjusted to 8.5.

Measuring procedures:

Placed in a 100-ml Erlenmeyer flask were 19 ml of one of the L-serine solutions and 0.2 ml of one of the PLP solution. Thiophenol (0.5 ml) was added, followed by incubation at 35° C. for 5 minutes. The cell suspension (0.5 ml) was added, followed by incubation for 60 minutes under shaking. Sixty minutes later, 1 ml of 35% hydrochloric acid was added to terminate the reaction, and the concentration of S-phenyl-L-cysteine in the solution was quantitated by HPLC. The amount (g) of S-phenyl-L-cysteine formed in an hour per gram of the dried cells was defined as S-phenyl-L-cysteine forming activity.

III. Method for the measurement of L-serine degrading activity

Prepared reagent 1: L-serine solutions

L-serine solutions of varied pHs in a range of from 7 to 11 were each prepared by dissolving 15.5 g of L-serine in about 450 ml of purified water, adjusting the pH of the resultant solution to the corresponding pH with an aqueous solution of sodium hydroxide and then adding purified water to give a total volume of 500 ml.

Prepared reagent 2: PLP solutions

PLP solutions of varied pHs in a range of from 7 to 11 were each prepared by dissolving 50 mg of pyridoxal phosphate in about 15 ml of purified water, adjusting the pH of the resultant solution to the corresponding pH with an aqueous solution of sodium hydroxide and then adding purified water to give a total volume of 20 ml.

Cell suspension:

Wet cells (1 g) were suspended in 10 ml of a PLP solution whose pH had been adjusted to 8.5.

Measuring procedures:

Placed in a 100-ml Erlenmeyer flask were 19 ml of one of the L-serine solutions and 0.2 ml of one of the PLP solution, followed by incubation at 35° C. for 5 minutes. The cell suspension (0.5 ml) was added, followed by incubation for 60 minutes under shaking. Sixty minutes later, 1 ml of 35% hydrochloric acid was added to terminate the reaction, and the concentration of L-serine in the solution was quantitated by HPLC. The amount (g) of L-serine degraded in-an hour per gram of the dried cells was defined as L-serine degrading activity.

TABLE 1

| | |
|---|---|
| Beef extract | 10 g |
| Polypepton | 10 g |
| NaCl | 5 g |
| Distilled water | 1 l |
| Adjusted to pH 7.0 with KOH. | |

TABLE 2

| | | | |
|---|---|---|---|
| $KH_2PO_4$ | 20 g | $K_2HPO_4$ | 20 g |
| $MgSO_4.7H_2O$ | 20 g | $(NH_4)_2SO_4$ | 15 g |
| Polypepton | 20 g | Yeast extract | 20 g |
| $CaCl_2.2H_2O$ | 0.4 g | $CuCl_2.2H_2O$ | 0.04 g |
| $CoCl_2.6H_2O$ | 0.04 g | $AlCl_3.6H_2O$ | 0.1 g |
| $H_3BO_3$ | 0.0005 g | $MnSO_4.5H_2O$ | 0.1 g |
| $ZnSO_4.7H_2O$ | 0.02 g | $Na_2MoO_4.2H_2O$ | 0.02 g |
| $FeSO_4.7H_2O$ | 0.4 g | Distilled water | 10 l |

Experiment 2

To an acidic solution of S-phenyl-L-cysteine obtained by dissolving 4.5 g of S-phenyl-L-cysteine in 100 ml of 3% hydrochloric acid, activated carbon "PMSX" (trade name, product of Mitsui Pharmaceuticals, Inc.) was added to a concentration of 1.7% so that an activated-carbon-added mixture was prepared. This procedure was additionally repeated twice to provide three activated-carbon-added mixtures in total. They were heated at 50° C., 70° C. and 80° C., respectively, for 20 hours. Further, a solution which had been prepared likewise except for the omission of the activated carbon was similarly heated at 80° C. for 20 hours. A portion of each mixture or solution was sampled periodically to measure the optical purity of S-phenyl-L-cysteine. Changes in the optical purity along the passage of time are shown in FIG. 2.

Method for the analysis of the optical purity of S-phenyl-L-cysteine

From the areas of peaks of the D-isomer and L-isomer of S-phenyl-L-cysteine in an HPLC analysis conducted using an optical resolution chromatography column "TSKgel Enantio L1" (trade name, product of TOSOH CORPORATION), the optical purity was determined in accordance with the following formula:

$$\text{Optical purity } (\%) = \frac{L(\text{area}) - D(\text{area})}{L(\text{area}) + D(\text{area})} \times 100$$

Conditions for optical resolution HPLC:

Column: "TSKgel Enantio L1" (trade name, product of TOSOH CORPORATION)

Mobile phase: 0.5 mM $CuSO_4$/acetonitrile =80/20

Temperature: 40° C.

Flow rate: 0.7 ml/min

Detection: 254 nm UV

EXAMPLE 1

A cell mass of *Escherichia coli* MT-10242 was obtained in a similar manner to Experiment 1. The cells so obtained had tryptophan synthase activity sufficient to synthesize 5 g of tryptophan in an hour per gram of dry cells.

To 500 g of an aqueous solution containing 3% of L-serine, 3.1% of thiophenol, 1% of ammonium chloride and 25 ppm of pyridoxal phosphate and having a pH of 9.0 (adjusted with NaOH), the centrifuged cells were added to a concentration of 0.7% as calculated based on dry cells.

The resultant mixture was stirred at 35° C. for 15 hours under a nitrogen gas atmosphere. The molar yield of S-phenyl-L-cysteine so formed was 85% based on L-serine.

After completion of the reaction, concentrated. hydrochloric acid was added to the reaction mixture to adjust its pH to 0.5. Ten grams of activated carbon ("PM-SX", trade name, product of Mitsui Pharmaceuticals, Inc.) were added, followed by heating at 50° C. for 3 hours. During the heating, the reaction mixture was sparged with air at the average aeration rate of 0.1 l/hr. Filtration was then conducted and the filtrate was adjusted to pH 3 with NaOH. After cooling the filtrate to 10° C., filtration was conducted so that crystals of S-phenyl-L-cysteine were separated. After drying the crystals, 20 g of S-phenyl-L-cysteine were obtained.

An elemental analysis of the thus-obtained crystals were conducted. Found: C: 54.48%, H: 5.69%, N: 7.64%, S: 15.57% (calculated: C: 54.82%, H: 5.58%, N: 7.11%, S: 16.24%).

As a result of an MS spectrum analysis, m/z=197 was detected as a parent peak. By an IR spectrum analysis, stretching vibrations of $NH_3^+$ and COOH were observed at 2900 $cm^{-1}$ and higher. Around 1620–1200 $cm^{-1}$, stretching and deformation vibrations of $NH_3^+$, $COO^-$ and alkyl groups, said vibrations being specific to an amino acid, were observed. Further, out-of-plane deformation vibrations of a mono-substituted benzene were observed at 735 and 689 $cm^{-1}$.

Signal assignment results on an NMR spectrum were consistent with the structure of S-phenyl-L-cysteine.

Further, the existence of a C-S bond was confirmed by a Raman spectrum analysis.

Moreover, by an HPLC analysis using the optical resolution chromatography column "TSKgel Enantio Li" (trade name; product of TOSOH CORPORATION), the crystals were confirmed to have the stereostructure of the L-isomer and an optical purity of 100%.

From the results of the above instrumental analyses, the crystals so obtained were confirmed to be S-phenyl-L-cysteine.

EXAMPLE 2

A cell mass of *Escherichia coli* MT-10242 was obtained in a similar manner to Experiment 1. To 500 g of an aqueous solution containing 6% of L-serine, 6.2% of thiophenol and 25 ppm of pyridoxal phosphate and having a pH of 9.5 (adjusted with NaOH), the cells were added to a concentration of 0.8% as calculated based on dry cells. The resultant mixture was stirred at 35° C. for 20 hours under a nitrogen gas atmosphere. During this stirring, the stirring power was controlled at 16 W per liter of the reaction mixture. The molar yield of S-phenyl-L-cysteine so formed was 87% based on the charged L-serine.

After completion of the reaction, concentrated hydrochloric acid was added to the reaction mixture to adjust its pH to 0.5. Purified water (500 g) then added to completely dissolve precipitated crystals of S-phenyl-L-cysteine. Ten grams of activated carbon ("PM-SX", trade name, product of Mitsui Pharmaceuticals, Inc.) were added, followed by heating at 50° C. for 3 hours. During the heating, the reaction mixture was sparged with air at the average aeration rate of 1.0 l/hr. Filtration was then conducted and the filtrate was adjusted to pH 3 with NaOH. After cooling the filtrate to 10° C., filtration was conducted so that crystals of S-phenyl-L-cysteine were separated. After drying the crystals, 40 g of S-phenyl-L-cysteine were obtained. Their optical purity was 100%.

EXAMPLE 3

A cell mass of *Escherichia coli* MT-10242 was obtained in a similar manner to Experiment 1.

To 500 g of an aqueous solution containing 10% of L-serine, 10% of thiophenol and 25 ppm of pyridoxal phosphate and having a pH of 10.0 (adjusted with NaOH), the cells were added to a concentration of 0.9% as calculated based on dry cells. The resultant mixture was stirred at 35° C. for 20 hours under a nitrogen gas atmosphere. During this stirring, the stirring power was controlled at 10 W per liter of the reaction mixture. The molar yield of S-phenyl-L-cysteine so formed was 85% based on the charged L-serine.

EXAMPLE 4

A cell mass of *Escherichia coli* MT-10242 was obtained in a similar manner to Experiment 1.

To 500 g of an aqueous solution containing 3% of L-serine, 3.1% of thiophenol and 25 ppm of pyridoxal phosphate and having a pH of 10.5 (adjusted with NaOH), the cells were added to a concentration of 0.7% as calculated based on dry cells. The resultant mixture was stirred at 35° C. for 15 hours under a nitrogen gas atmosphere. The molar yield of S-phenyl-L-cysteine so formed was 70% based on the charged L-serine.

What is claimed is:

1. A process for producing S-phenyl-L-cysteine by reacting thiophenol and L-serine under the action of tryptophan synthase, wherein said reaction is conducted in an aqueous solution of a pH in a range of from 9.0 to 10.5.

2. The process according to claim 1, wherein said reaction is conducted in an aqueous solution of pH 9.0 to pH 10.0.

3. The process according to claim 1, wherein said reaction is conducted at a temperature of from 20° to 60° C.

4. The process according to claim 1, wherein said tryptophan synthase is that obtained from *Escherichia coli*.

5. The process according to claim 4, wherein said tryptophan synthase is that obtained from *Escherichia coil* FERM BP-20.

6. The process according to claim 1, wherein said tryptophan synthase is that obtained from *Neurospora crassa*.

7. The process according to claim 6, wherein said tryptophan synthase is that obtained from *Neurospora crassa* ATCC 14692.

8. The process according to claim 1, wherein the concentration of L-serine in said aqueous solution is from 1 to 10 wt. %.

9. The process according to claim 1, wherein the concentration of thiophenol in said aqueous solution is not higher than 10 wt. %.

10. The process according to claim 1, wherein said reaction is conducted in the presence of 0.1 to 100 ppm of pyridoxal phosphate.

11. The process according to claim 1, wherein said reaction is conducted in the presence of an ammonium salt at a concentration of from 0.1 to 5 wt.%.

12. A process for producing S-phenyl-L-cysteine, which comprises the following steps:

(a) adjusting the pH of an enzymatic reaction mixture containing crystals of S-phenyl-L-cysteine to an acidic level so that the crystals of S-phenyl-L-cysteine precipitated in said reaction mixture are dissolved;

(b) adding activated carbon to said reaction mixture, in which S-phenyl-L-cysteine is dissolved, and then maintaining the resultant reaction mixture while aerating the same with an oxygen-containing gas, whereby a solid matter and unreacted thiophenol are adsorbed on said activated carbon and unreacted thiophenol not adsorbed on said activated carbon is insolubilized;

(c) removing said activated carbon and insolubilized matter from said reaction mixture to obtain an S-phenyl-L-cysteine solution; and (d) adding an alkali to said S-phenyl-L-cysteine solution to precipitate crystals of S-phenyl-L-cysteine, and then recovering said crystals of S-phenyl-L-cysteine.

13. The process according to claim 12, wherein the enzymatic reaction mixture is obtained by reacting thiophenol and L-serine under the action of tryptophan synthase in an aqueous solution having a pH in a range of from 9.0 to 10.5, thereby obtaining a reaction mixture containing S-phenyl-L-cysteine so formed.

14. The process according to claim 12, wherein the pH of the enzymatic reaction mixture is adjusted to 1.5 or lower than 1.5.

15. The process according to claim 12, wherein the pH of the S-phenyl-L-cysteine solution in step (d) is adjusted to a range of from 2.5 to 6.0.

* * * * *